Figure 1:
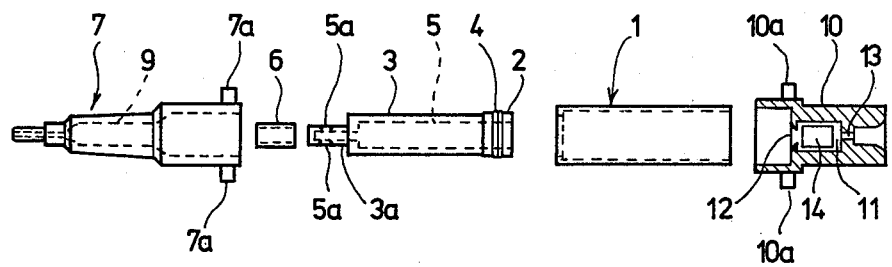

United States Patent [19]

Van Brugge

[11] 4,204,539

[45] May 27, 1980

[54] PUMPS AND SYRINGES

[76] Inventor: Mathews Van Brugge, 105a Stokes Valley Rd., Stokes Valley, Lower Hutt, New Zealand

[21] Appl. No.: 32,468

[22] Filed: Apr. 23, 1979

[51] Int. Cl.$^2$ ............................................... A61D 7/00
[52] U.S. Cl. ..................................... 128/223; 128/234
[58] Field of Search ............... 128/223, 234, 235, 224, 128/237, 218 R, 218 G

[56] References Cited

U.S. PATENT DOCUMENTS

| 3,682,175 | 8/1972 | Halter | 128/223 |
|---|---|---|---|
| 4,020,838 | 5/1977 | Phillips et al. | 128/223 |
| 4,033,346 | 7/1977 | Phillips et al. | 128/223 |

*Primary Examiner*—John D. Yasko

*Attorney, Agent, or Firm*—Scully, Scott, Murphy & Presser

[57] ABSTRACT

The invention is concerned primarily with a piston action pump/syringe usable for veterinary work in particular (but not confined to this use) for the dispensing of metered doses of liquids or pastes, and includes a cylindrical body reciprocally housing a piston end of a co-axial plunger which extends outwardly from the body, the plunger and piston end having a common bore through which the body contents can be dispensed. The outlet end of the plunger, which is provided with a nozzle, has a novel one way valve permitting egress of the body contents and the end of the body remote from the plunger has a novel one way inlet valve for ingress of liquid or paste from a connected supply source. Preferably the invention includes an operating hand grip for the pump/syringe of one piece plastics construction.

17 Claims, 7 Drawing Figures

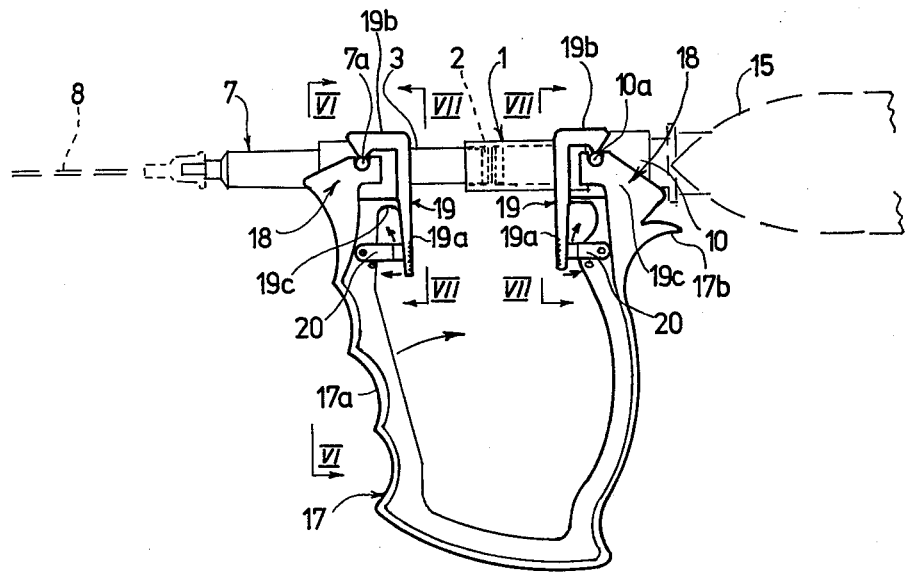
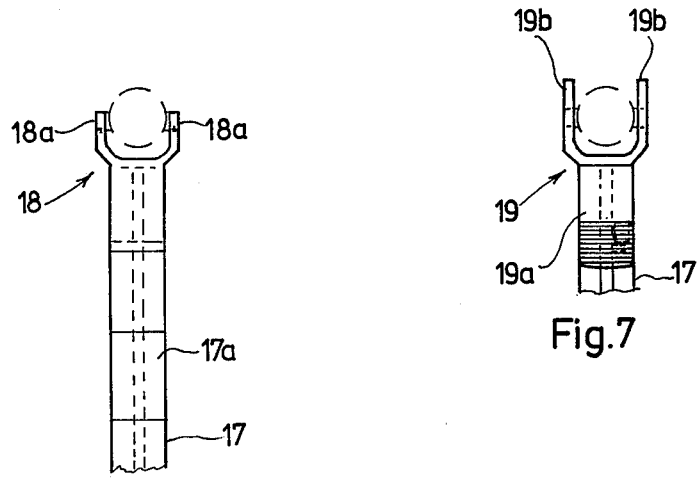
Fig.5
Fig.6
Fig.7

4,204,539

PUMPS AND SYRINGES

This invention relates to pumps and syringes and more particularly relates to piston action pumps and syringes for the dispensing of liquids.

An object of this invention is to provide a pump/syringe of relatively simple construction and employing simple valving means permitting effective operation of the pump/syringe.

Another object of this invention is to provide a pump/syringe which may have a variety of applications in the dispensing of liquids.

Other and more particular objects and advantages of the invention will become apparent from the ensuing description.

According to one aspect of this invention, there is provided a piston action pump/syringe for liquids comprising a cylindrical tubular body reciprocally housing a piston end of a co-axial plunger which extends outwardly from said body, said plunger and piston end having a common bore through which the body contents can be dispensed and the outlet end of said plunger having a one way valving means including a movable sleeve or skirt part located about said outlet end and an outlet thereof so as to permit egress only of said body contents, and the end part of the body remote from the plunger being provided with one way valving means for ingress only of liquid to the body from a supply source, said body valving means including an elongate member loosely housed in an enlarged bore for longitudinal reciprocal movement between a non-sealable small valve opening to the body interior at one end and a valve opening at the opposite end communicating with a liquid supply source and sealable by the respective elongate member end on the body contents being pressurised by inward movement of the plunger, outward movement of the plunger relative to the body causing suction therewithin to draw the elongate member off the valve opening to the supply source and towards the non-sealable opening and permit liquid from the supply source to by-pass the elongate member into the body.

Figure 2:
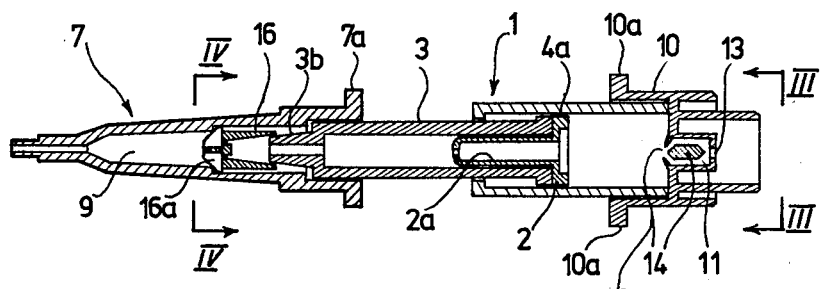

According to a second aspect of this invention, there is provided a hand grip and operating device for effecting operation of the pump and/or syringe of the preceding paragraph, comprising a unitary substantially U-shaped hand grip member of a strong and at least partially resilient material permitting the free end parts of such U-shaped member to be squeezable towards each other against an inherent spring bias, said end parts being each provided with engaging means for engagement with the pump/syringe at parts which are movable towards and away from each other in operation of the pump/syringe. Preferred aspects of the invention will now be described by way of example and with reference to the accompanying drawings, in which:

FIG. 1 is an exploded and part broken view of the pump/syringe in accordance with the invention, FIG. 2 is a longitudinal sectional view of an assembled alternative construction of pump/syringe in accordance with the invention.

Figure 3:
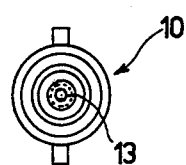
Figure 4:
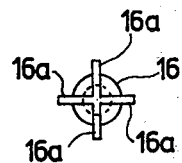

FIG. 3 is a rear end view of the syringe of FIG. 2, as viewed in the direction of arrow III—III, FIG. 4 is an end view of the valving means at the outlet end of the plunger in the construction according to FIG. 2, FIG. 5 is a side elevational view of the pump/syringe of either FIG. 1 or FIG. 2 assembled and provided with hand grip and operating means, FIG. 6 is a front end view of the hand grip and operating means of FIG. 1, as viewed in the direction of arrows VI—VI, and FIG. 7 is a view in the direction of either of the arrows VII—VII of FIG. 1 showing the inside appearance of the engaging means. The pump/syringe is preferably of all or substantially all plastics construction and may be intended to be a disposable pump/syringe for such as as medicinal and veterinary work, although the invention is not confined to this aspect and may have other applications as herein mentioned. Where the invention is to be used for medicinal and veterinary work, it is of course desirable that the plastics materials utilised are capable of sterilisation.

Referring firstly to FIG. 1 of the drawings, the body 1 may be of simple cylindrical tube form, preferably transparent so that the contents can be viewed, and the piston 2 with the attached plunger 3 (which can be separately formed or formed in one piece) is reciprocally housed in such body 1 with the piston 2 or plunger inner end part defining a piston 2 provided with an annular resilient sealing ring or like member 4 located in an annular groove of the piston or plunger inner end part 2 and arranged for sealing engagement with the body inner wall. The sealing ring 4 is preferably manufactured from such as a neoprene or like material and may have a double external annular rib for maximum sealing. The piston 2 and plunger 3 are provided with a common bore 5 through which the body contents can be expelled and the outlet end part of the plunger 3 is provided with a simple one way valving means which may be similar to a bicycle tube valve with a short closed end cylindrical stem portion 3a having one or more side ports 5a in communication with the plunger bore 5 and over which a sleeve 6 of resilient material such as rubber is located. A detachable hollow nozzle piece 7 is preferably arranged for fitment over the plunger outer end part and valve portion and such nozzle piece 7 can have a plain nozzle end for the ejection of a stream of liquid or may be arranged as a bayonet end portion 7a as common provided on surgical and veterinary hypodermic syringes and on which a surgical needle 8 can be detachably engaged. The nozzle piece 7 may alternatively be replaceable by a spray nozzle attachment or be adapted to receive a spray nozzle attachment of any suitable kind and whereby the body contents can be sprayed instead of jetted.

With the provision of a nozzle piece 7 (either a jetting or needle receiving nozzle piece or a spray nozzle piece), as an alternative to the bicycle valve arrangement at the outlet end of the plunger 3, the plunger outer end part can be provided with an integral thin and thus resilient annular skirt portion arranged to peripherally contact the inner surface of the nozzle piece 7 surrounding the bore 9 thereof so as to be normally in sealing engagement therewith, and the plunger outlet end portion is closed at the end but provided with at least one but preferably a plurality of side opening ports or apertures in communication with the plunger bore 5 and the arrangement provides that liquid forced through such side apertures will exert pressure on and deform the skirt so that the liquid can be ejected from the nozzle piece 7.

The rear end of the body 1, that is the end remote from the plunger outlet end and nozzle piece 7, is preferably arranged to be closed by a valve unit including a stepped cylindrical valve body 10 having part in close fit engagement over the pump/syringe body rear end, and an extension part with an enlarged cylindrical bore 11 having a non-sealable opening 12 at one end opening to the pump/syringe body 1 and an inlet opening 13 at its opposite end opening to a source of liquid supply, there being a cylindrical solid plastics member 14 loosely and slidably located in the enlarged bore 11 so that it is movable from one end to the other according to the pressure exerted thereon and with the end directed towards the sealable inlet opening 13 being arranged to close such opening when the body contents are pressurised by movement of the plunger 3 inwardly relative to the body 1.

The valve unit extension part can be adapted to receive an end portion of a flexible tube or pipe line leading to a liquid supply reservoir, or can be adapted to receive directly the neck of a rigid or collapsible reservoir (as shown at 15 in FIG. 5).

The body 1, nozzle piece 7 and valve body 10, as well as the plunger 3, can all be formed independently and then press fitted together, and (except the plunger 3) can be welded, adhered or otherwise permanently secured together or can be separable for cleaning if required.

Referring now to FIGS. 2, 3 and 4, of the drawings, in an alternative construction of the pump/syringe of this invention the piston 2 is formed separately from the plunger 3 and whereas the plunger 3 may be of a hard or high density plastics material (the nozzle piece 7 and rear end valve body 10 may be of the same material), the piston 2 can be of lesser density and have a slight inherent resilience to have a hollow shank part 2a arranged as a press fit within the plunger 3, and preferably to have an integrally formed annular rib 4a forming a seal ring. Additionally the rear end valve unit can differ from that described with reference to FIG. 1 by provision of a body 10 having the general form illustrated in FIGS. 2 and 3 with integral concentric cylindrical tube parts with which two or three different supply tube or container neck sizes can be engaged. Also, the valving means at the outlet end of the plunger can comprise the construction according to FIGS. 2 and 4 with a hollow thin walled cylindrical valve member 16 of a resilient plastics material and arranged to locate as a sealing fit over a frusto-conical outlet end portion 3b of the plunger 3, the valve member 16 being closed at its end remote from the plunger and provided with spacer fins or like projections 16a locating the valve member 16 in sliding engagement centrally within the nozzle piece 7; the valve member 16 being permitted a small amount of longitudinal movement between the plunger 3 and an abutment within the nozzle piece 7 so as to be movable longitudinally from sealing engagement with the plunger end portion 3b (when filling of the pump/syringe takes place) to non-sealing position off the plunger end portion 3b on ejection of the pump/syringe contents, the contents by-passing the fins or projections 16a.

In one preferred form of the invention, a hand grip and operating means is provided for the pump/syringe and such hand grip and operating means may comprise a resilient U-shaped member having a forward end part arranged for detachable engagement with the nozzle piece 7 and a similar rear end part arranged for detachable engagement with the valve unit body 10, the arrangement providing that the two legs of the U-shaped hand grip member can be squeezed together to urge the plunger 3 into the body 1 to eject the body contents, and when pressure is released on the hand grip member inherent resilience in the material utilised in the construction of such hand grip member will bias the leg portions of the U-shape outwardly back to their original position in withdrawing the plunger 3 outwardly relative to the body 1 to cause suction within the body 1 and draw a further supply of liquid from the supply source through the inlet valve means at the rear end of the pump/syringe.

Referring now to FIGS. 5, 6 and 7, of the drawings, the U-shaped (in side elevation) hand grip member, generally indicated by the arrow 17, is preferably formed integrally from a strong substantially rigid plastics material having some inherent resilience or springiness, e.g., such as a reinforced polystyrene, an acetone or polycarbonate material. The forward outer side of the front leg of the U-shape can be provided with corrugations, ribs or indentations 17a to prevent a user's fingers slipping therefrom in operation, and the rear upper part of the rear leg can be provided with a hooked abutment 17b to comfortably fit a user's hand.

The upper free end portions of the front and rear legs of the U-shaped hand grip and operating member 17 are provided with pump/syringe engaging means so as to be each engaged in non-moving or substantially non-moving (a slight relative pivoting moving may take place) relationship with relevant spaced parts of the pump/syringe, and the hand grip and operating means in accordance with the invention is preferably detachably engageable with the pump/syringe to permit disposal of one syringe and substitution of another. Accordingly, in one form of the invention and as illustrated by way of example, each upper free end part of each leg of the U-shaped member 17 is provided with a preferably integrally formed cradle 18 and spring clip arrangement 19, each cradle 18 being generally of U-shape (when viewed endwise) with upstanding side walls 18a and between which respective forward and rearward parts of the pump/syringe 4, i.e., the nozzle 7 or plunger 3 and the body 1, can locate; the U-formations of the cradles 18 being aligned fore and aft for reception of the pump/syringe.

In providing the detachable engagement between the pump/syringe and the hand grip and operating member 17, the nozzle piece 7 and rear valve body 10 can each be provided with opposed projections or trunnions 7a and 10a engageable by the spring clip 19. Each spring clip 19 can be a lever operated member of generally inverted L-formation when viewed in side elevation, the foot 19b of which can extend over and prevent disengagement of the respective trunnion or like projection 7a or 10a. Preferably such clip or lever member 19 is integrally formed with the cradle part 18 with a thin connecting strip 19c forming a springy hinge medially of the longer leg 19a of the L and below the line of the pump/syringe so that the clip foot part 19b is normally biased over the projection or trunnion 7a or 10a of the respective pump/syringe part. The terminal parts of the clip foot 19b and cradle walls 18a at the slots may be bevelled and the opposing lead in portions to the slots of the cradles 18 may be similarly bevelled in opposition so that the pump/syringe trunnions 7a and 10a can be snapped into position against the spring bias of the respective clip members 19, and the pump/ syringe subsequently released when required to be disposed of or exchanged by squeezing the lower part of the longer leg 19a of each L-shaped clip member 19 below its hinge strip 19c towards the respective upper end portion of the hand grip member 17. The L-shaped clip members 19 may be bi-furcated above the hinge connection 19c so that the pump/syringe 4 may locate between the bi-furcations and the foot clip parts 19b are locatable over both trunnions 7a and 10a. Preferably also the L-shaped clip members 19 are located on the inner sides of the two cradles 18 and the hand grip member 17 so that in handling the assembly the clip members 19 are not likely to be accidentally released. Also pivoted safety catch members 20 can be provided on the upper parts of the hand grip member 17 to lock the clip members 19 in position.

The invention may have applications as previously indicated for medicinal and veterinary purposes in the dispensing of medicines and the like, but with the hand grip combination it is also envisaged that, particularly with the spray attachment, the invention may have application as a garden spray or household spray (as an alternative to the employment of aerosol and like spray devices), or may have a novel application as a toy water-pistol.

Particular forms of the invention have been described and illustrated by way of example, but it will be appreciated that other variations of and modifications to the invention can take place without departing from the scope of the appended claims.

I claim:

1. A piston action pump/syringe for liquids comprising a cylindrical tubular body reciprocally housing a piston end of a co-axial plunger which extends outwardly from said body, said plunger and piston end having a common bore through which the body contents can be dispensed and the outlet end of said plunger having a one way valving means including a movable sleeve or skirt part located about said outlet end and an outlet thereof so as to permit egress only of said body contents, and the end part of the body remote from the plunger being provided with one way valving means for ingress only of liquid to the body from a supply source, said body valving means including an elongate member loosely housed in an enlarged bore for longitudinal reciprocal movement between a non-sealable small valve opening to the body interior at one end and a valve opening at the opposite end communicating with a liquid supply source and sealable by the respective elongate member end on the body contents' being pressurised by inward movement of the plunger, outward movement of the plunger relative to the body causing suction therewithin to draw the elongate member off the valve opening to the supply source and towards the non-sealable opening and permit liquid from the supply source to by-pass the elongate member into the body.

2. A pump/syringe as claimed in claim 1 wherein the plunger and piston end are formed integrally of plastics material with a separately formed seal ring being provided in an annular groove in the piston end.

3. A pump/syringe as claimed in claim 1 wherein the piston end is formed independently of the plunger and subsequently engaged therewith, and said piston end is formed of a plastics material having some inherent resilience and includes an integrally forming annular rib constituting a seal ring.

4. A pump/syringe as claimed in claim 1 wherein the outlet end of the body is provided with a hollow nozzle end piece having a bayonet end portion adapted to detachably receive a surgical needle.

5. A pump/syringe as claimed in claim 1 wherein the outlet end of the body is provided with a hollow nozzle end piece and a spray nozzle attachment is provided for detachable engagement with said nozzle end piece.

6. A pump/syringe as claimed in claim 1 wherein the one way valving means for egress of the body contents comprises a sleeve of rubber or like resilient material located as a sealing fit over a cylindrical outer end portion of the plunger, said outer end portion being closed at its outer end and provided with a bore communicating with the plunger bore and at least one side aperture communicating with the end portion bore but being sealable by the resilient sleeve.

7. A pump/syringe as claimed in claim 1 wherein the outlet end of the body is provided with a hollow nozzle end piece and the one way valving means for egress of the body contents comprises an integral thin and flexible resilient annular skirt portion provided on the plunger outer end part and arranged for peripheral normal sealing contact with the inner surface of the nozzle piece, the plunger outer end portion being closed at the end but provided with at least one side opening port or aperture communicating with the plunger bore.

8. A pump/syringe as claimed in claim 1 wherein the outlet end of the body is provided with a hollow nozzle end piece and the one way valving means for egress of the body contents comprises a hollow thin walled cylindrical valve member arranged to locate as a sealing fit over a frusto-conical outlet end portion of the plunger, the valve member being closed at its end remote from the plunger and provided with spacer fins or like projections locating the valve member in sliding engagement centrally within the nozzle piece; the valve member being permitted some longitudinal movement between sealing engagement with the plunger outlet end portion and a non-sealing position at an abutment within the nozzle piece.

9. A pump/syringe as claimed in claim 1 and in combination with a hand grip and operating device for effecting operation of said pump/syringe, said device comprising a unitary substantially U-shaped hand grip member of a strong and at least partially resilient material permitting the free end parts of such U-shaped member to be squeezable towards each other against an inherent spring bias, said end parts being provided with engaging means for engagement with the pump/syringe at parts which are movable towards and away from each other in operation of the pump/syringe.

10. A combination as claimed in claim 9 wherein the free end part of each leg of the hand grip and operating device is provided with a cradle and complementary clipping arrangement, one cradle being arranged to receive the body part of the pump/syringe and the other cradle being arranged to receive an external part of or connected to an outlet end part on the plunger of the pump/syringe, the clipping arrangements locking the respective pump/syringe parts in the cradles.

11. A combination as claimed in claim 10 wherein each cradle of the hand grip and operating device has aligned recess or socket portions arranged to receive complementary aligned and opposed lateral projections or trunnions provided on the respective parts of the pump/syringe.

12. A combination as claimed in claim 11 wherein each clipping arrangement of the hand grip and operating device includes a lever operated clip member which is spring biased to have a part normally arranged to extend over and be biased over the respective cradle recess or socket portions and the pump/syringe lateral projections or trunnions when engaged therein.

13. A combination as claimed in claim 12 wherein said clip member parts are bevelled at their terminal ends and/or opposing lead in portions to the cradle recesses or sockets are bevelled to permit the pump/syringe projections or trunnions to be snapped into position against the clip member spring bias.

14. A combination as claimed in claim 12 wherein each clip member is mounted for hinging movement relative to the respective free end part of each leg, each clip member being of substantially inverted L-shape in side elevation with the hinge connection medially of the longer leg of the L-shape and the foot of the L-shape being bifurcated and being the part extending over and biased toward the cradle recesses or sockets.

15. A combination as claimed in claim 14 wherein each clip member is formed integrally with the respective cradle part and connected thereto by a thin connecting strip forming a springy hinge.

16. A combination as claimed in claim 9 wherein all parts of the hand grip and operating device are integrally formed from a substantially rigid plastics material having some inherent resilience or springiness.

17. A combination as claimed in claim 12 wherein the hand grip member is provided with safety catch means to lock the clip members against movement.

* * * * *